United States Patent
Dershem

(10) Patent No.: US 7,868,113 B2
(45) Date of Patent: *Jan. 11, 2011

(54) LOW SHRINKAGE POLYESTER THERMOSETTING RESINS

(75) Inventor: Stephen M Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 586 days.

This patent is subject to a terminal disclaimer.

(21) Appl. No.: 11/786,027

(22) Filed: Apr. 11, 2007

(65) Prior Publication Data

US 2008/0251935 A1   Oct. 16, 2008

(51) Int. Cl.
*C08F 4/80* (2006.01)
*C07C 69/76* (2006.01)
*C07C 69/74* (2006.01)

(52) U.S. Cl. .................. 526/285; 526/319; 526/346; 526/313; 560/90; 560/121; 560/122; 560/127

(58) Field of Classification Search ............... 526/285, 526/319, 346, 313; 560/90, 121, 122, 127
See application file for complete search history.

(56) References Cited

U.S. PATENT DOCUMENTS

| | | | |
|---|---|---|---|
| 3,336,266 A | 8/1967 | McConnell et al. | |
| 3,379,041 A * | 4/1968 | Schmid et al. ............ | 70/456 R |
| 3,739,041 A | 6/1973 | Schmid et al. | |
| 3,918,393 A | 11/1975 | Hahn | |
| 4,363,907 A | 12/1982 | Hefner et al. | |
| 4,395,462 A | 7/1983 | Polmanteer | |
| 4,483,898 A | 11/1984 | Schonhorn et al. | |
| 4,540,829 A | 9/1985 | Hefner, Jr. | |
| 4,560,768 A | 12/1985 | Hefner et al. | |
| 4,623,696 A | 11/1986 | Mabrey et al. | |
| 4,753,982 A | 6/1988 | Hefner, Jr. | |
| 4,774,267 A | 9/1988 | Weintraub | |
| 4,777,209 A | 10/1988 | Hefner, Jr. | |
| 4,968,738 A | 11/1990 | Dershem | |
| 5,045,127 A | 9/1991 | Dershem et al. | |
| 5,064,480 A | 11/1991 | Dershem et al. | |
| 5,128,746 A | 7/1992 | Pennisi et al. | |
| 5,155,177 A | 10/1992 | Frihart | |
| 5,232,962 A | 8/1993 | Dershem et al. | |
| 5,306,333 A | 4/1994 | Dershem et al. | |
| 5,358,992 A | 10/1994 | Dershem et al. | |
| 5,376,721 A | 12/1994 | McGarry et al. | |
| 5,403,389 A | 4/1995 | Dershem | |
| 5,428,105 A | 6/1995 | McGarry et al. | |
| 5,430,112 A | 7/1995 | Sakata et al. | |
| 5,437,964 A | 8/1995 | Lapin et al. | |
| 5,447,988 A | 9/1995 | Dershem et al. | |
| 5,489,641 A | 2/1996 | Dershem | |
| 5,567,761 A | 10/1996 | Song | |
| 5,596,669 A | 1/1997 | Murphy et al. | |
| 5,646,241 A | 7/1997 | Dershem et al. | |
| 5,707,782 A | 1/1998 | Economy et al. | |
| 5,714,086 A | 2/1998 | Osuna et al. | |
| 5,717,034 A | 2/1998 | Dershem et al. | |
| 5,718,941 A | 2/1998 | Dershem et al. | |
| 5,753,748 A | 5/1998 | Dershem et al. | |
| 5,861,111 A | 1/1999 | Dershem et al. | |
| 5,880,170 A | 3/1999 | Imura et al. | |
| 5,891,566 A | 4/1999 | Sakumoto et al. | |
| 5,969,036 A | 10/1999 | Dershem | |
| 5,973,166 A | 10/1999 | Mizori et al. | |
| 6,034,194 A | 3/2000 | Dershem | |
| 6,034,195 A | 3/2000 | Dershem | |
| 6,063,828 A | 5/2000 | Ma et al. | |
| 6,121,358 A | 9/2000 | Dershem et al. | |
| 6,187,886 B1 | 2/2001 | Husson, Jr. et al. | |
| 6,211,320 B1 | 4/2001 | Dershem et al. | |
| 6,265,530 B1 | 7/2001 | Herr et al. | |
| 6,281,314 B1 | 8/2001 | Tong et al. | |
| 6,313,189 B1 | 11/2001 | Wenz et al. | |
| 6,316,566 B1 | 11/2001 | Ma et al. | |
| 6,355,750 B1 | 3/2002 | Herr | |
| 6,403,757 B1 * | 6/2002 | Yabuta et al. ............ | 528/310 |
| 6,423,780 B1 | 7/2002 | Dershem et al. | |
| 6,429,281 B1 | 8/2002 | Dershem et al. | |
| 6,451,929 B1 | 9/2002 | Smits et al. | |
| 6,482,899 B2 * | 11/2002 | Ohashi et al. ............ | 525/486 |

(Continued)

FOREIGN PATENT DOCUMENTS

EP            1834969         9/2007

(Continued)

OTHER PUBLICATIONS

International Search Report for related PCT Application No. PCT/US06/07943, Sep. 25, 2006.
Adamson, "Review of CSP and Flip Chip Underfill Processes and When To Use the Right Dispensing Tools For Efficient Manufacturing", *Paper Presented at GlobalTRONICS Technology Conference*,Singapore 2002, 1-6.
DSM, "Hybrane (TM) DSM's new dendritic polymers", *DSM New Business Development product literature 99-1c* 1999, 1-10.
Klang, "Radiation-curable Hyperbranched Polyester Acrylates", *PCI Magazine* Apr. 2007, 98-101.

*Primary Examiner*—Michael M Bernshteyn
(74) *Attorney, Agent, or Firm*—The Law Office of Jane K. Babin; Jane K. Babin

(57) ABSTRACT

The invention is based on the discovery that a certain polyester compounds are useful as b-stageable adhesives for the microelectonic packaging industry. The polyester compounds described herein contain ring-opening or ring-forming polymerizable moieties and therefore exhibit little to no shrinkage upon cure. In addition, there are provided well-defined b-stageable adhesives useful in stacked die assemblies. In particular, there are provided assemblies wherein the b-stageable adhesive encapsulates a portion of the wiring members contained within the bondline gap between the stacked die.

23 Claims, 4 Drawing Sheets

U.S. PATENT DOCUMENTS

| | | |
|---|---|---|
| 6,521,731 B2 | 2/2003 | Dershem et al. |
| 6,577,013 B1 | 6/2003 | Glenn et al. |
| 6,620,946 B2 | 9/2003 | Dershem et al. |
| 6,699,929 B2 | 3/2004 | Musa et al. |
| 6,743,852 B2 | 6/2004 | Dershem et al. |
| 6,750,301 B1 | 6/2004 | Bonneau et al. |
| 6,777,027 B2 | 8/2004 | Daly et al. |
| 6,790,597 B2 | 9/2004 | Dershem et al. |
| 6,825,245 B2 | 11/2004 | Dershem et al. |
| 6,831,132 B2 | 12/2004 | Liu et al. |
| 6,852,814 B2 | 2/2005 | Dershem et al. |
| 6,916,856 B2 | 7/2005 | Dershem |
| 6,946,523 B2 | 9/2005 | Dershem et al. |
| 6,960,636 B2 | 11/2005 | Dershem et al. |
| 6,963,001 B2 | 11/2005 | Dershem et al. |
| 7,102,015 B2 | 9/2006 | Dershem et al. |
| 7,157,587 B2 | 1/2007 | Mizori et al. |
| 7,176,044 B2 | 2/2007 | Forray et al. |
| 7,199,249 B2 | 4/2007 | Liu et al. |
| 7,208,566 B2 | 4/2007 | Mizori et al. |
| 7,228,161 B2 | 6/2007 | Chin |
| 7,230,055 B2 | 6/2007 | Musa |
| 7,285,613 B2 | 10/2007 | Dershem et al. |
| 7,309,724 B2 | 12/2007 | Dershem et al. |
| 7,517,925 B2 | 4/2009 | Dershem et al. |
| 7,678,879 B2 | 3/2010 | Dershem |
| 2002/0002238 A1 | 1/2002 | Laplante et al. |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0083436 A1 | 5/2003 | Deitch |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0129438 A1 | 7/2003 | Becker et al. |
| 2003/0166746 A1 | 9/2003 | Zhou et al. |
| 2003/0178138 A1 | 9/2003 | Tsukagoshi |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0067606 A1 | 4/2004 | Fehr et al. |
| 2004/0068027 A1 | 4/2004 | Daly et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0110859 A1 | 6/2004 | Biro et al. |
| 2004/0122168 A1 | 6/2004 | Murray |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0027082 A1 | 2/2005 | Narayan-Sarathy et al. |
| 2005/0107542 A1 | 5/2005 | Liu et al. |
| 2005/0136620 A1 | 6/2005 | Dershem et al. |
| 2005/0137277 A1 | 6/2005 | Dershem et al. |
| 2005/0267254 A1 | 12/2005 | Mizori et al. |
| 2005/0272888 A1 | 12/2005 | Dershem et al. |
| 2006/0009578 A1 | 1/2006 | Dershem |
| 2006/0063014 A1 | 3/2006 | Forray |
| 2006/0069232 A1 | 3/2006 | Dershem |
| 2006/0089447 A1 | 4/2006 | Robertson et al. |
| 2006/0142517 A1 | 6/2006 | Dershem |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dersham |
| 2008/0257493 A1 | 10/2008 | Dershem |
| 2008/0262191 A1 | 10/2008 | Mizori |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |

FOREIGN PATENT DOCUMENTS

| | | | |
|---|---|---|---|
| JP | 57-036125 A | | 2/1982 |
| JP | 2003002919 A | * | 1/2003 |
| JP | 2004037475 | | 2/2004 |
| WO | WO-8604073 | | 7/1986 |
| WO | WO-9406862 | | 3/1994 |
| WO | WO-2004060330 | | 7/2004 |
| WO | WO-2005003231 | | 1/2005 |
| WO | WO-2005121190 | | 12/2005 |
| WO | WO-2007100329 | | 9/2007 |
| WO | WO-2008077141 | | 6/2008 |
| WO | WO-2008124797 | | 10/2008 |
| WO | WO-2008130894 | | 10/2008 |
| WO | WO-2010019832 | | 2/2010 |

* cited by examiner

An example of stacked die using melt-through-wires wafer back coating

LOW SHRINKAGE POLYESTER THERMOSETTING RESINS

FIELD OF THE INVENTION

The present invention relates to low shrinkage, b-stageable thermosetting adhesive compositions, methods of preparation and uses therefor. In particular, the present invention relates to b-stageable thermosetting compounds and compositions containing polymerizable polyester compounds.

BACKGROUND OF THE INVENTION

Adhesive compositions, particularly conductive adhesives, are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards. Adhesives useful for electronic packaging applications typically exhibit properties such as good mechanical strength, curing properties that do not affect the component or the carrier, and rheological properties compatible with application to microelectronic and semiconductor components.

Recently, there has been an increased interest in b-stageable adhesives. A b-stageable material is a material that is usually dispensed onto a substrate as a liquid, then is b-staged to achieve a first solid phase. In this first solid phase the material acts like a thermoplastic, i.e., the material flows at an elevated temperature. At an even higher temperature, the material irreversibly crosslinks and becomes a thermoset material. The transition from the thermoplastic stage to the second solid phase is thermosetting. However, prior to that, the material behaves similarly to a thermoplastic material. Thus, such a material would permit low lamination temperatures while providing high thermal stability. In addition, b-stageable adhesives eliminate many of the storage, handling, dispensing, and processing issues that exist when dispensing an adhesive in a flowable form.

Moreover, a continuing challenge in the microelectronics packaging industry is the issue of shrinkage upon cure of the adhesives contained within the package. In many cases, the adhesive(s) used in a package shrinks when cured, thereby creating stress at the various interfaces inside the package. This leads to package failure and device failure and/or unreliability. Accordingly, there is a continuing need for b-stageable adhesives in the electronic packaging industry, and a particular need for adhesives with little to no shrinkage upon cure.

SUMMARY OF THE INVENTION

The invention is based on the discovery that a certain polyester compounds are useful as b-stageable adhesives for the microelectonic packaging industry. The polyester compounds described herein contain ring-opening or ring-forming polymerizable moieties and therefore exhibit little to no shrinkage upon cure.

In one embodiment, there are provided compounds having the structure:

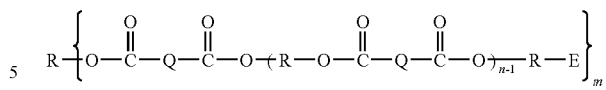

wherein:
R and Q are each independently substituted or unsubstituted aliphatic or alkenyl, aryl, or heteroaryl;
each E is independently a ring-opening or ring-forming polymerizable moiety; and
m is 3 or 4; and
n is 1 to about 10.

In another embodiment, there are provided adhesive compositions including at least one of the above described compounds, and at least one curing initiator.

In yet another embodiment, there are provided b-stageable die-attach pastes including
a) 0.05 weight percent to about 98 weight percent (wt %) of at least one of the above-described compounds, or combinations thereof, based on total weight of the composition,
b) 0 to about 90 wt % of a filler;
d) 0.05 wt % to about 5 wt % of at least one curing initiator, based on total weight of the composition;
e) 0.05 wt % to about 4 wt %, of at least one coupling agent, based on total weight of the composition.

In another embodiment, there are provided assemblies including a first article permanently adhered to a second article by a cured aliquot of the die-attach pastes according to the invention.

In another embodiment, there are provided methods for attaching a first article to a second article. Such methods can be performed, for example, by
(a) applying an aliquot of the adhesive composition of the invention to the first article,
(b) bringing the first and second article into intimate contact to form an assembly wherein the first article and the second article are separated only by the adhesive composition applied in (a), and thereafter,
(c) subjecting the assembly to conditions suitable to cure the adhesive composition.

In another embodiment, there are provided methods for attaching a semiconductor die to a substrate. Such methods can be performed, for example, by
(a) applying the die attach paste of the invention to the substrate and/or the microelectronic device,
(b) subjecting the substrate and/or the microelectronic device to conditions suitable to form a b-staged curable film,
(c) exposing the b-staged curable film to temperature conditions suitable to melt the film,
(d) bringing the substrate and the device into intimate contact to form an assembly wherein the substrate and the device are separated only by the die-attach paste, and
(e) subjecting the b-staged curable film to conditions suitable to cure the melted film.

In another embodiment of the invention, there are provided well-defined b-stageable adhesives useful in stacked die assemblies. In particular, the invention provides assemblies wherein the b-stageable adhesive encapsulates a portion of the wiring members contained within the bondline gap between the stacked die. In other words, the b-stageable adhesive has the ability to flow through (i.e., encapsulate) the wires as the adhesive fills the bondline gap, thereby preventing any mold compound from covering the wires. This situation is quite advantageous since it is known that mold compound encapsulation of the wiring members creates a CTE (coefficient of thermal expansion) mismatch. The b-stageable adhesives of the invention include at least one polyester compound described herein.

In one embodiment of the invention, there is provided a semiconductor die assembly including:
a) a substrate having wiring members extending from pads on the substrate for electrically connecting a die to the substrate,
b) a bottom die having a bottom surface and a top surface, wherein the bottom surface contacts the substrate, and wherein the top surface of the bottom die has electrical pads for attaching a wiring member from the substrate, and wherein a first die-attach adhesive is disposed between the substrate and the bottom die,
c) a first top die having a bottom surface and a top surface, wherein the first top die is positioned above the bottom die so that the bottom surface of the first top die is facing the top surface of the bottom die, thereby creating a first bondline gap between the bottom die and the top die, wherein a portion of the wiring members extending from the electrical pads on the top surface of the bottom die are located within the first bondline gap, and
d) a second die-attach adhesive disposed between the bottom die and the top die, thereby filling the first bondline gap and creating a first bondline, and encapsulating the portion of the wiring members located within the first bondline.

DETAILED DESCRIPTION OF THE INVENTION

Figure 1:
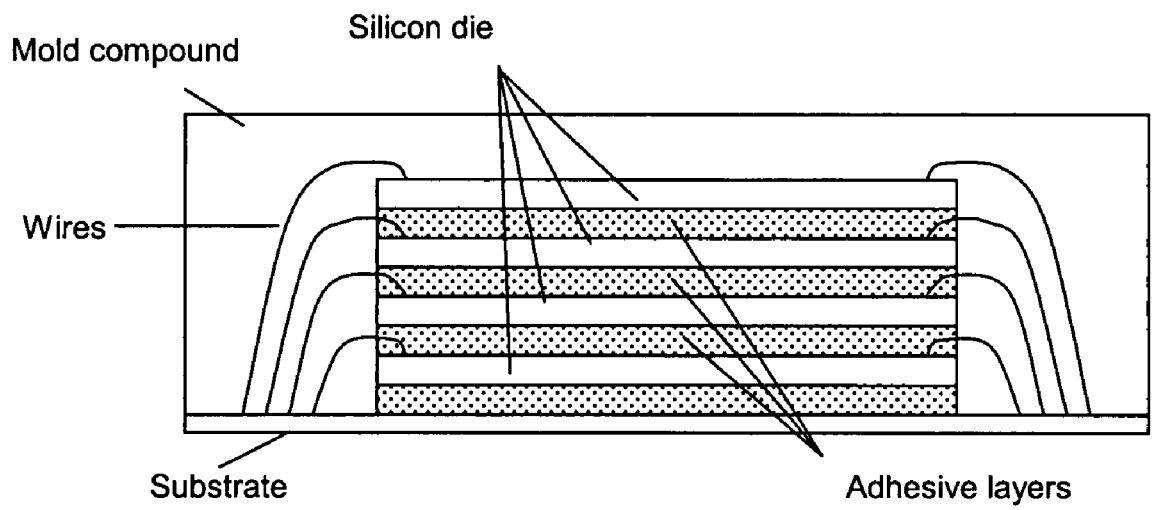
FIG. 1 depicts a cross-section of a semiconductor die assembly according to the invention. In this Figure, the assembly is a stacked die assembly containing 4 die, with a b-stageable adhesive according to the invention disposed between each die.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

The invention is based on the discovery that certain polyester compounds are useful as b-stageable adhesives for the microelectonic packaging industry. In one embodiment of the invention there are provided compounds having the structure:

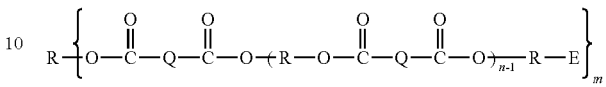

wherein:
R and Q are each independently substituted or unsubstituted aliphatic or alkenyl, aryl, or heteroaryl;
each E is independently a ring-opening or ring-forming polymerizable moiety; and
m is 3 or 4; and
n is 1 to about 10.

As used herein, "aliphatic" refers to any alkyl, alkenyl, cycloalkyl, or cycloalkenyl moiety.

As used herein, "alkyl" refers to straight or branched chain hydrocarbyl groups having from 1 up to about 500 carbon atoms. Whenever it appears herein, a numerical range, such as "1 to 500" or "$C_1$-$C_{500}$", refers to each integer in the given range; e.g., "$C_1$-$C_{500}$ alkyl" means that an alkyl group may comprise only 1 carbon atom, 2 carbon atoms, 3 carbon atoms, etc., up to and including 500 carbon atoms, although the term "alkyl" also includes instances where no numerical range of carbon atoms is designated). "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—O—, —C(O)—, —S—, —S(O)$_2$—, —OC(O)—O—, —NR—C(O)—, —NR—C(O)—NR—, —OC(O)—NR—, wherein R is H or lower alkyl, acyl, oxyacyl, carboxyl, carbamate, sulfonyl, sulfonamide, sulfuryl, and the like.

As used herein, "cycloalkyl" refers to cyclic ring-containing groups typically containing in the range of about 3 up to about 20 carbon atoms, and "substituted cycloalkyl" refers to cycloalkyl groups further bearing one or more substituents as set forth above.

As used herein, "aryl" refers to aromatic groups having in the range of 6 up to 20 carbon atoms and "substituted aryl" refers to aryl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 20 carbon atoms and "substituted heterocyclic" refers to heterocyclic groups further bearing one or more substituents as set forth above. The term heterocyclic is also intended to refer to heteroaromatic moieties. As used herein, "alkenyl" refers to straight or branched chain hydrocarbyl groups having at least one carbon-carbon double bond, and having in the range of 2 up to about 500 carbon atoms, and "substituted alkenyl" refers to alkenyl groups further bearing one or more substituents as set forth above.

As used herein, "alkylene" refers to a divalent alkyl moiety, and "oxyalkylene" refers to an alkylene moiety containing at least one oxygen atom instead of a methylene ($CH_2$) unit. "Substituted alkylene" and "substituted oxyalkylene" refer to alkylene and oxyalkylene groups further bearing one or more substituents as set forth above.

As used herein, "arylene" refers to a divalent aryl moiety. "Substituted arylene" refers to arylene moieties bearing one or more substituents as set forth above.

As used herein, the term "polymerizable moiety" refers to a moiety that undergoes ring-opening polymerization, such as, for example, epoxy, oxetane, oxazoline, benzoxazine, and the like. In other embodiments, the term "polymerizable moiety" refers to a moiety that forms a ring upon polymerization, such as, for example, cyanate esters, propargyl ethers, and the like.

As used herein, the term "crosslinkable" refers to any moiety that has the ability to crosslink with another moiety. As used herein, the term "crosslink" refers to the attachment of two or more polymer chains by bridges of an element, a molecular moiety, or a compound. In general, crosslinking of the compounds of the invention takes place upon heating. As cross-linking density is increased, the properties of a material will be changed from thermoplastic to thermosetting.

In certain embodiments, R is a substituted or unsubstituted cycloalkyl having from 5 to about 20 carbon atoms. In other embodiments, R is a substituted or unsubstituted cycloalkyl having from 5 to about 12 carbon atoms. In some embodiments, R is a substituted or unsubstituted cyclopentyl, cyclohexyl, norbornyl, tetracyclododecyl, or dicyclopentadienyl.

In some embodiments, R is a substituted or unsubstituted aliphatic. In some embodiments, R is $C_2$ to about $C_{500}$ aliphatic. In other embodiments, R is $C_2$ to about $C_{250}$ aliphatic. In still other embodiments, R is $C_2$ to about $C_{100}$ aliphatic. In some embodiments, R is $C_2$ to about $C_{50}$ aliphatic. In still further embodiments, R is $C_{36}$ aliphatic.

A wide variety of aryl and heteroaryl moieties are contemplated for Q in the practice of the invention. In some embodiments, Q is a substituted or unsubstituted aryl or heteroaryl having from 6 to about 20 carbon atoms. In other embodiments, Q is a substituted or unsubstituted phenyl or naphthyl. In further embodiments, Q is a substituted or unsubstituted cycloalkyl, such as, for example, norbornyl.

In some embodiments, Q is a substituted or unsubstituted aliphatic or alkenyl. In some embodiments, Q is $C_2$ to about $C_{500}$ aliphatic. In other embodiments, Q is $C_2$ to about $C_{250}$ aliphatic. In still other embodiments, Q is $C_2$ to about $C_{100}$ aliphatic. In some embodiments, Q is $C_2$ to about $C_{50}$ aliphatic or alkenyl. In still further embodiments, Q is $C_{36}$ aliphatic.

A wide variety of ring opening and/or ring forming polymerizable moieties are contemplated for use in the practice of the invention. Ring opening moieties include, for example, epoxy (such as glycidyl ethers of aliphatic alcohols, glycidyl esters, cylcoaliphatic epoxies such as cycloaliphatic epoxies derived from oligomers of cyclopentadiene, and the like) oxetane, oxazoline, benzoxazine, and the like. Ring forming moieties include, for example, cyanate ester, propargyl ether, and the like.

The compounds of the invention are readily prepared according to organic chemistry techniques well-known to those skilled in the art. For example, the esters and described herein are typically prepared by condensation of the appropriate acid and alcohols to the corresponding ester under acid catalysis; or alternatively, the compounds are prepared via transesterification under acid or base catalysis. Another synthetic route to the compounds described herein is a condensation reaction of the appropriate alcohols and acid chlorides in the presence of a tertiary amine. Exemplary compounds according to the invention are set forth below:

Compound 1

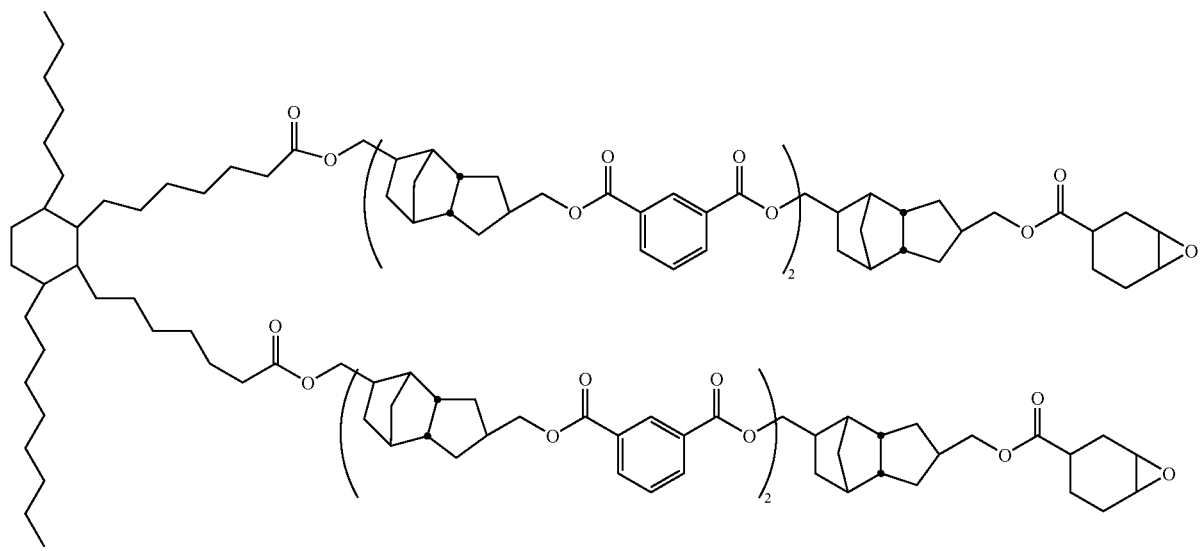

Compound 2
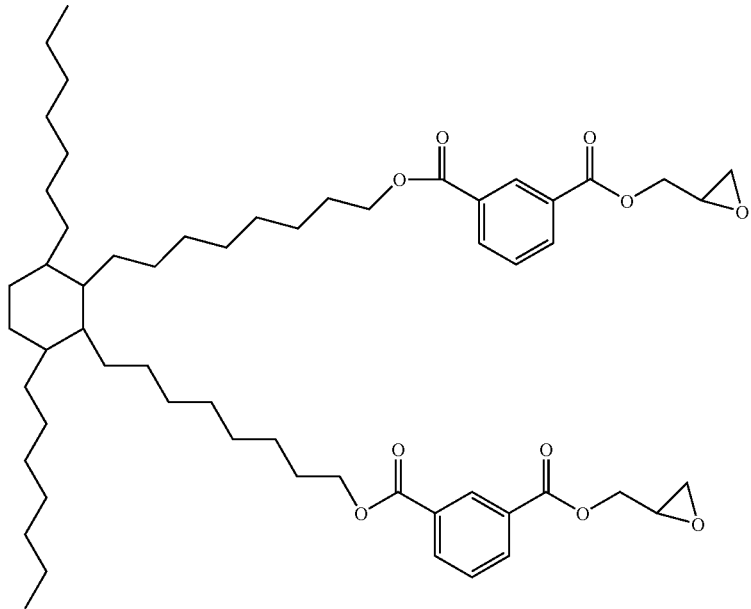
Compound 3
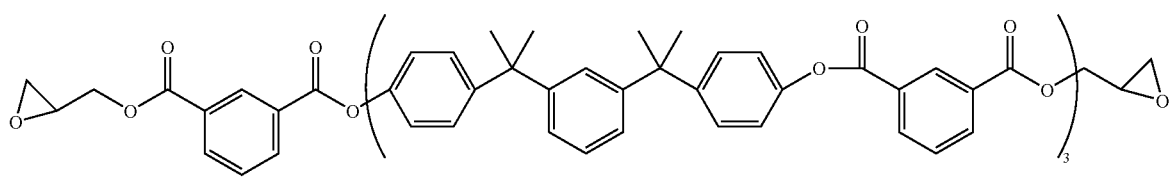
Compound 4
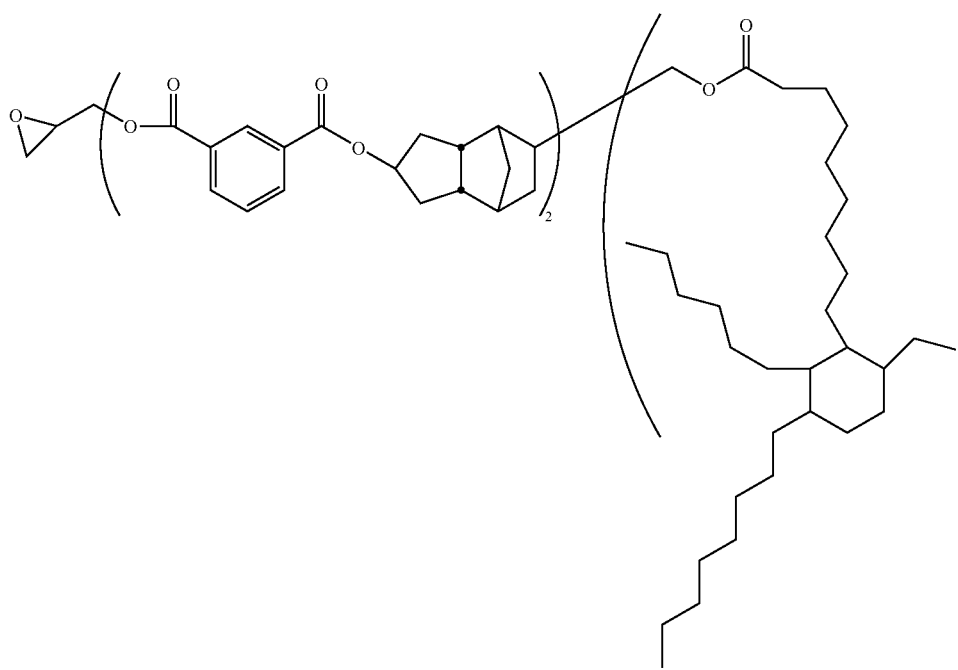

-continued

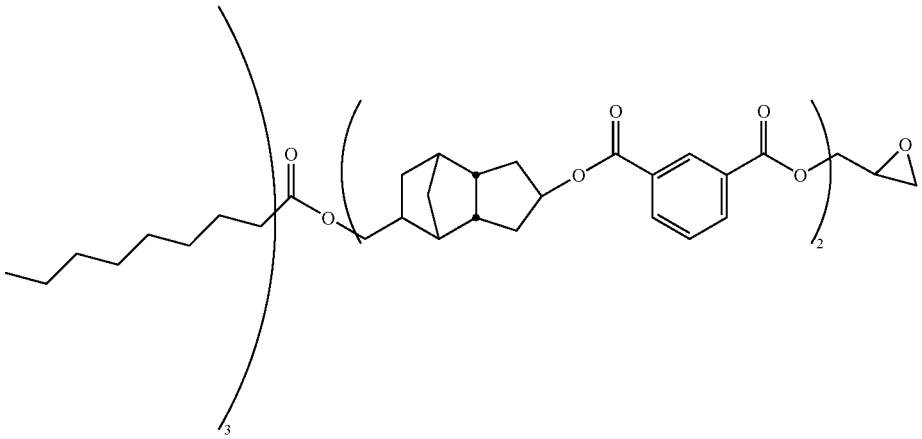

The polyester compounds of the invention may be used independently in adhesive compositions, or may be combined with other adhesive compounds and resins. In one embodiment, a polyester compound of the invention may be used as the sole thermoset monomer of the adhesive composition. In another embodiment, the polyester compound of the invention may be combined with other thermoset monomers to make a fully formulated adhesive. In still another embodiment, the polyester compounds of the invention may be combined with thermoplastic polymers and/or oligomers to form interpenetrating networks.

In one embodiment, there is provided an adhesive composition including at least one invention polyester compound and optionally at least one curing initiator.

In some embodiments, the polyester compound is present in the composition from 2 weight percent to about 98 weight percent (wt %) based on total weight of the composition.

In addition to the functional polyesters described herein, curatives can be present in the composition from 2 weight percent to about 80 weight percent (wt %) based on total weight of the composition. Examples of curatives include, but are not limited to, phenols, anhydrides, phenylacetates, thiols, and isocyanates.

The at least one curing initiator is typically present in the composition from 0.05 wt % to about 5 wt % based on total weight of the composition. Certain catalysts contemplated, include for example, compounds which can be employed to catalyze the reaction between a phenolic hydroxyl group and a vicinal epoxide group include, for example, tertiary amines such as, triethylamine, tripropylamine, tributylamine; 2-methylimidazole (such as, for example, the Curezol™ imidazoles available from Air Products), N-methylmorpholine, combinations thereof and the like; quaternary ammonium compounds such as, benzyl trimethyl ammonium chloride, tetrabutylammonium chloride, combinations thereof and the like; phosphines such as triphenylphosphine, tributylphosphine, trilaurylphosphine, trichlorobutylphosphine, trinaphthylphosphine, and the like; and phosphonium compounds such as, ethyltriphenylphosphonium chloride, ethyltriphenylphosphonium bromide, ethyltriphenylphosphonium iodide, ethyltriphenylphosphonium phosphate, ethyltriphenylphosphonium acetate.acetic acid complex, tetrabutylphosphonium chloride, tetrabutylphosphonium bromide, tetrabutylphosphonium iodide, tetrabutylphosphonium phosphate, tetrabutylphosphonium acetate.acetic acid complex, butyltriphenylphosphonium tetrabromobisphenate, butyltriphenylphosphonium bisphenate, butyltriphenylphosphonium bicarbonate, combinations thereof and the like. In addition, for applications outside the microelectronic packaging industry, catalysts contemplated for use include alkali metal hydroxides such as, sodium hydroxide, potassium hydroxide, lithium hydroxide, combinations thereof and the like.

In another embodiment of the invention, there are provided die-attach pastes including 0.05 weight percent to about 98 weight percent (wt %) of at least one polyester compound described herein, or combinations thereof, based on total weight of the composition; optionally, 0.05 wt % to about 90 wt % of at least one additional compound selected from the group consisting of acrylates, methacrylates, maleimides, vinyl ethers, vinyl esters, styrenic compounds, and allyl functional compounds, and the like, based on total weight of the composition; 0 to about 90 wt % of a filler; 0.05 wt % to about 5 wt % of at least one curing initiator, based on total weight of the composition; and 0.05 wt % to about 4 wt %, of at least one coupling agent, based on total weight of the composition. In some embodiments, the additional compound includes, for example, phenolics epoxies, novalac epoxies, imides, cyanate esters, vinyl ethers, vinyl esters, amides, siloxanes, cyanoacrylates, and the like, or combinations thereof.

In one embodiment, there is provided a b-stageable die-attach paste including:
  a) 0.05 weight percent to about 98 weight percent (wt %) based on total weight of the composition, of a polyester compound having the structure:

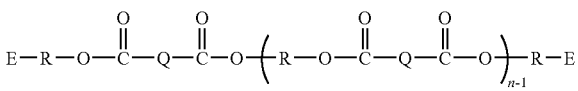

wherein:
  R and Q are each independently substituted or unsubstituted aliphatic or alkenyl, aryl, or heteroaryl;
  each E is independently a ring-opening or ring-forming polymerizable moiety; and
  n is 1 to about 10;

b) 0 to about 90 wt % of a filler;

d) 0.05 wt % to about 5 wt % of at least one curing initiator, based on total weight of the composition;

e) 0.05 wt % to about 4 wt %, of at least one coupling agent, based on total weight of the composition.

As used herein, "b-stageable" means that the adhesive has a first solid phase followed by a thermoplastic stage at elevated temperature, followed by another solid irreversibly crosslinked phase at an even higher temperature. The transition from the thermoplastic stage to the second solid phase is thermosetting. However, prior to that, the material behaves similarly to a thermoplastic material. Thus, such an adhesive allows for low lamination temperatures while providing high thermal stability.

Fillers contemplated for use in the practice of the present invention are typically electrically conductive, thermally conductive, and/or fillers which act primarily to modify the rheology of the resulting composition. Examples of suitable electrically conductive fillers are silver, copper, nickel, palladium, graphite, and the like. Examples of suitable thermally conductive fillers which can be employed in the practice of the present invention include graphite, aluminum nitride, silicon carbide, boron nitride, diamond dust, alumina, and the like. Compounds which act primarily to modify rheology include polysiloxanes (such as polydimethyl siloxanes) silica, fumed silica, alumina, titania, calcium carbonate, polytetrafluoroethylene, and the like.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates or compounds that contain a copolymerizable group and a chelating ligand (e.g., phosphine, mercaptan, acetoacetate, and the like). In some embodiments, the coupling agents contain both a co-polymerizable function (e.g., glycidyl ether, cycloaliphatic epoxy, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste.

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive composition.

In general, these b-stageable compositions will cure within a temperature range of 80-220° C., and curing will be effected within a length of time of less than 1 minute to 180 minutes. The b-stageable die-attach paste may be preapplied onto either a semiconductor die or onto a substrate. As will be understood by those skilled in the art, the time and temperature curing profile for each adhesive composition will vary, and different compositions can be designed to provide the curing profile that will be suited to the particular industrial manufacturing process.

In certain embodiments, the adhesive compositions may contain compounds that lend additional flexibility and toughness to the resultant cured adhesive. Such compounds may be any thermoset or thermoplastic material having a Tg of 50° C. or less, and typically will be a polymeric material characterized by free rotation about the chemical bonds, the presence of ether groups, and the absence of ring structures. Suitable such modifiers include polyacrylates, poly(butadiene), hydrogenated polybutadiene, polyTHF (polymerized tetrahydrofuran, also known as poly(1,4-butanediol)), CTBN (carboxy-terminated butadiene-acrylonitrile) rubber, and polypropylene glycol. When present, toughening compounds may be in an amount up to about 15 percent by weight of the total composition.

These compositions will perform within the commercially acceptable range for die attach adhesives. Commercially acceptable values for die shear for the adhesives on a 80×80 $mil^2$ silicon die are in the range of greater than or equal to 1 kg at room temperature, and greater than or equal to 0.5 kg at 260° C.

In yet another embodiment of the invention, there are provided assemblies of components adhered together employing the above-described b-stageable adhesive compositions and/or die attach pastes. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like. Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like. Organic substrates contemplated for use include polyamide, FR4, bismaleimide-triazine (BT), and the like.

In another embodiment of the invention, there are provided methods for attaching a first article to a second article. Such methods can be performed, for example, by (a) applying an aliquot of the adhesive composition of the invention to the first article, (b) bringing the first and second article into intimate contact to form an assembly wherein the first article and the second article are separated only by the adhesive composition applied in (a), and (c) subjecting the assembly to conditions suitable to cure the adhesive composition.

In another embodiment of the invention, there are provided methods for attaching a semiconductor die to a substrate. Such methods can be performed, for example, by (a) applying the b-stageable die attach paste of the invention to the substrate and/or the microelectronic device, (b) subjecting the substrate and/or the microelectronic device to conditions suitable to form a b-staged curable film, (c) exposing the b-staged curable film to temperature conditions suitable to melt the film, (d) bringing the substrate and the device into intimate contact to form an assembly wherein the substrate and the device are separated only by the die-attach paste, and (e) subjecting the b-staged curable film to conditions suitable to cure the melted film.

In some embodiments, the substrate is metal, such as, for example, copper, alloy 42, Ag-plated copper, and the like. In other embodiments, the substrate is Ni-plated copper, Pd-plated copper, Au-plated copper, Ni—Pd—Au-plated copper, and the like. In other embodiments, the substrate includes nickel, palladium, and gold.

In some embodiments, the substrate is organic, such as for example, polyamide, FR4, bismaleimide-triazine (BT), BT-glass, and the like.

It is understood that using the compounds and methods of the present invention, it is possible to prepare adhesives having a wide range of cross-link density by the judicious choice and amount of polyester compounds. The greater proportion of polyfunctional compounds reacted, the greater the cross-link density. If thermoplastic properties are desired, the adhesive compositions can be prepared from (or at least contain a higher percentage of) mono-functional compounds to limit the cross-link density. A minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

"Cross-linking," as used herein, refers to the attachment of two or more polymer chains by bridges of an element, a molecular group, or a compound. In general, crosslinking of the compounds of the invention takes place upon heating. As cross-linking density is increased, the properties of a material will be changed from thermoplastic to thermosetting.

In another embodiment of the invention, there are provided stacked die assemblies wherein the b-stageable die attach adhesive encapsulates a portion of the wiring members contained within the bondline gap between the stacked die. In other words, the b-stageable adhesive has the ability to flow through (i.e., encapsulate) the wires (prior to thermosetting) as the adhesive fills the bondline gap, thereby preventing any mold compound from covering the wires.

Figure 2:
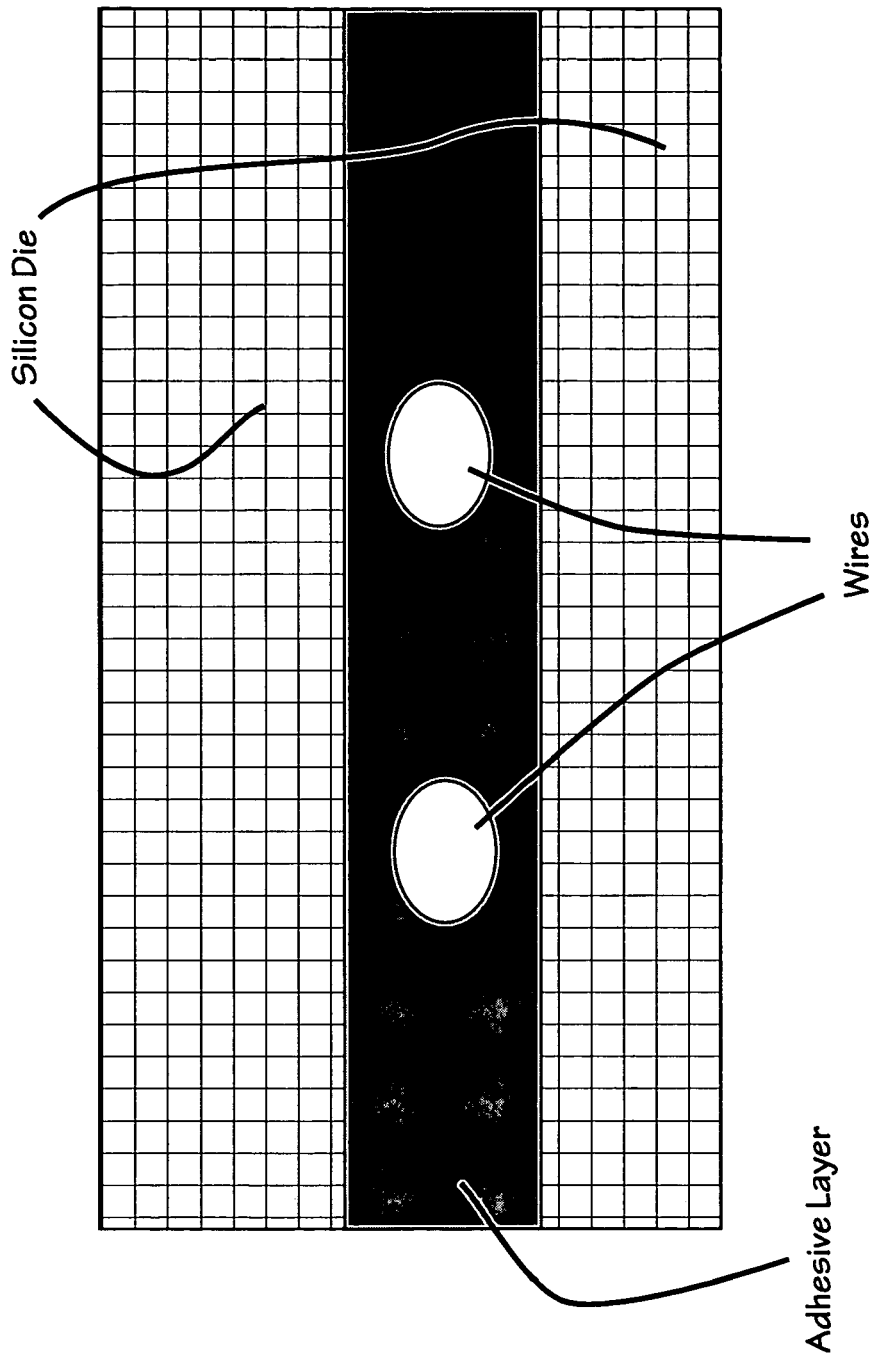
FIG. 2 is a cross-section in greater detail showing the adhesive of the invention encapsulating the gold wire bonds within the bondline, thereby preventing mold compound from flowing into the bondline and damaging the wire bonds.
Figure 3:
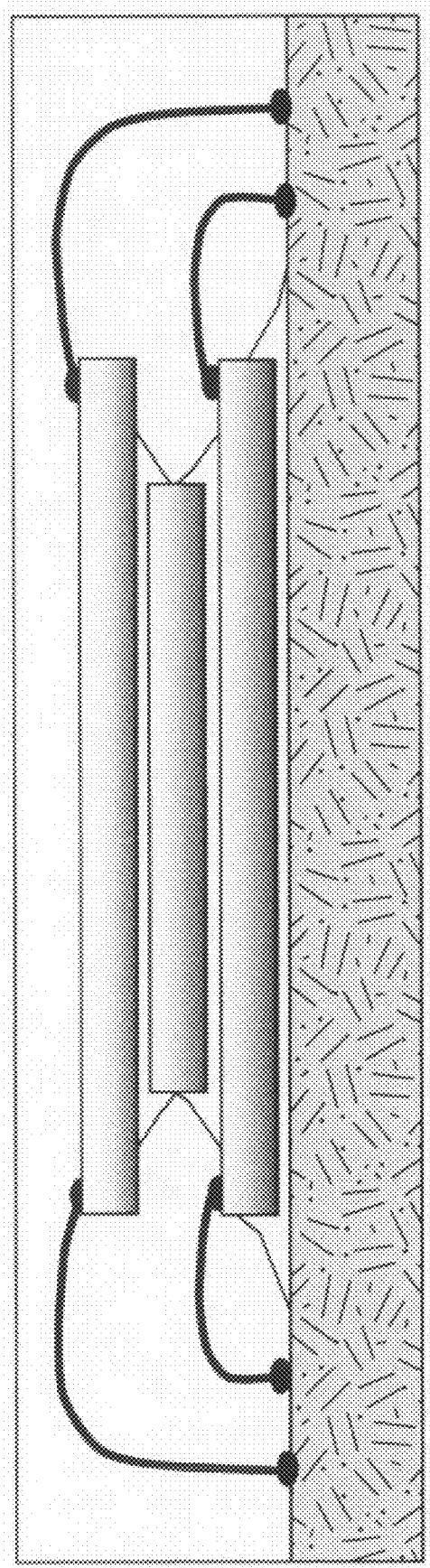
FIG. 3 depicts a stacked die package containing a dummy die. As shown in the Figure, the wire bonds are not encapsulated by the die attach adhesive, and therefore are susceptible to damage when the mold compound is applied to the package.
Figure 4:
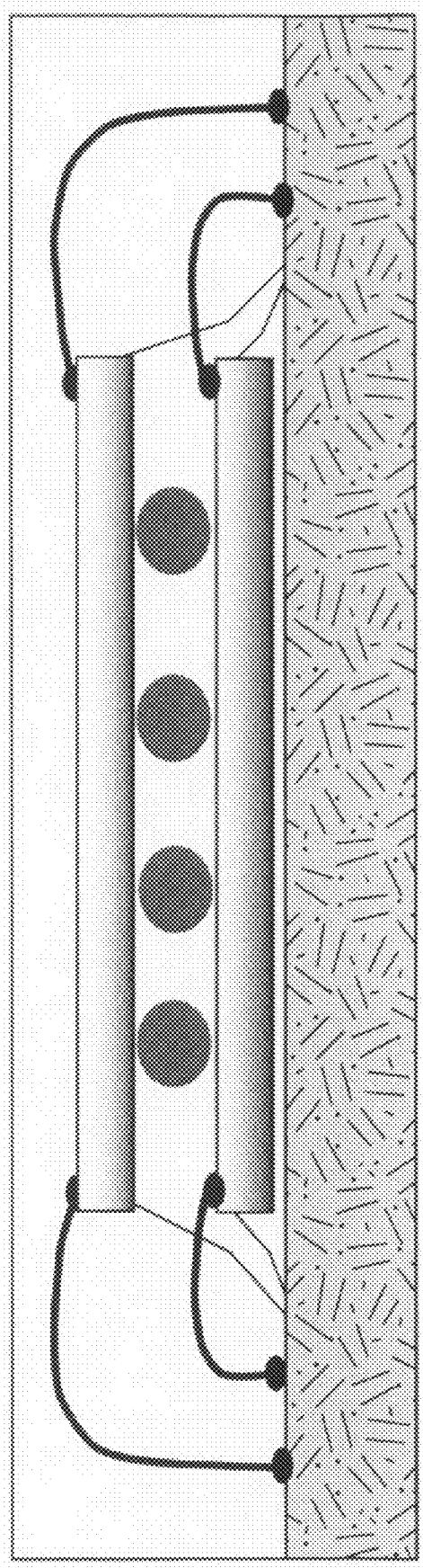
FIG. 4 depicts a stacked die package using spacer paste as die attach adhesive.

For example, FIG. 1-3 show cross-sectional views of an assembly containing 4 stacked die, with a well-defined b-stageable die attach adhesive described herein disposed between each of the die. In some embodiments, the bondline thickness is 1 to 10 mils. In other embodiments, the bondline thickness is 1 to 6 mils. In still other embodiments, the bondline thickness is 1 to 3 mils. In the assembly shown in FIGS. 1-3, the die thickness and bondline thickness is 3 mils. This clearly demonstrates that the b-stageable die attach adhesive described herein is useful for producing stacked die packages with very thin die and bondlines. In certain embodiments, the assembly includes 2 die. In other embodiments, the assembly includes 3 die. In other embodiments, the assembly includes 4 die.

The invention described herein has particular advantages over other stacked die assemblies using spacer pastes or dummy die. With respect to spacer pastes (see FIG. 6), the invention described herein provides uniform bondline thickness and die attach coverage. In addition, in contrast to assemblies using spacer pastes, there is no die shift and no overflowing to the die top (especially for thin die). Thus, the present invention is ideal for tight tolerance packages.

With respect to assemblies containing dummy die (see FIG. 5), the assemblies described herein have a significantly reduced bondline gap. In addition, the additional die attach process for the dummy die is eliminated, thus reducing all oven cure processes down to one (prior to molding).

The invention will now be further described with reference to the following non-limiting examples.

EXAMPLES

Example 1

Compound 1

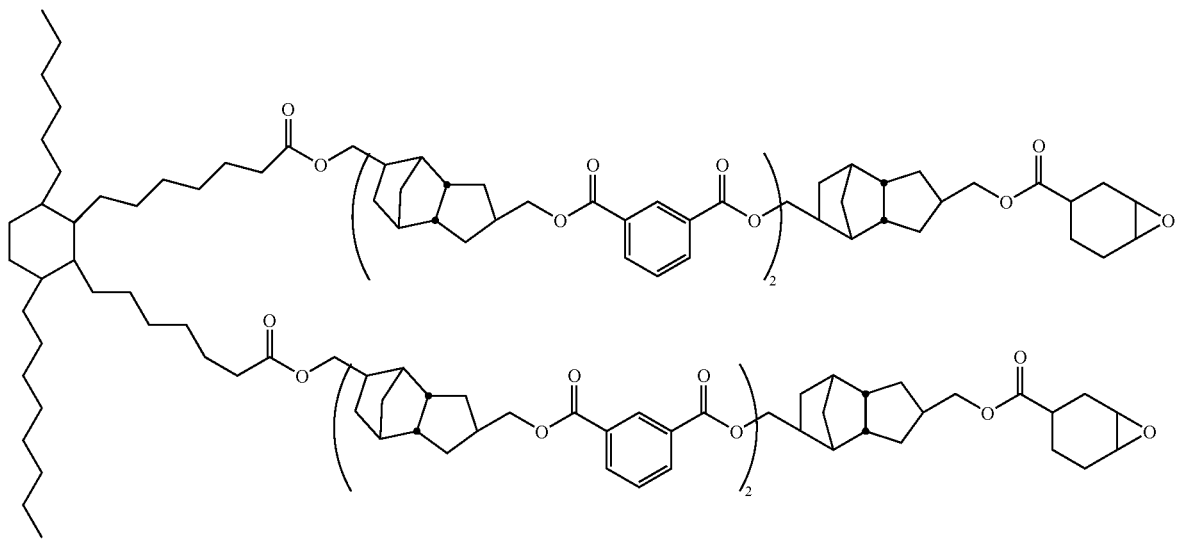

To a 500 mL flask was added isophthalic acid (33.2 g, 200 mmol), 4,8-bis(hydroxymethyl)tricyclo[5.2.1.0$^{2,6}$]decane (58.8 g, 300 mmol), Empol 1008 (hydrogenated dimmer acid, available from Cognis) (28.3 g, 50 mmol), and toluene (150 mL). The reaction mixture was heated to 70° C., at which time methanesulfonic acid (3 g) was added. The flask was equipped with a reflux condenser and Dean-Stark trap, and the reaction mixture was refluxed for 21 hrs yielding the expected amount of water (9.0 mL). After cooling, toluene (110 mL) and SiO$_2$ (10 g) were added to the flask and the mixture was stirred for 30 min. The mixture was then passed over SiO$_2$ (20 g). After removal of toluene by rotary evaporation, Dow ERL 4140 (17.2 g, 110 mmol) and DMAP (0.76 g) were added to the mixture. The Dean-Stark trap was filled with octane and an additional aliquot of octane (8 mL) was added to the reaction mixture, and the mixture was refluxed for 2.5 days. Removal of octane by rotary evaporation afforded Compound 1 (92.1 g, 74.4% yield) as a viscous, red-brown liquid.

Example 2

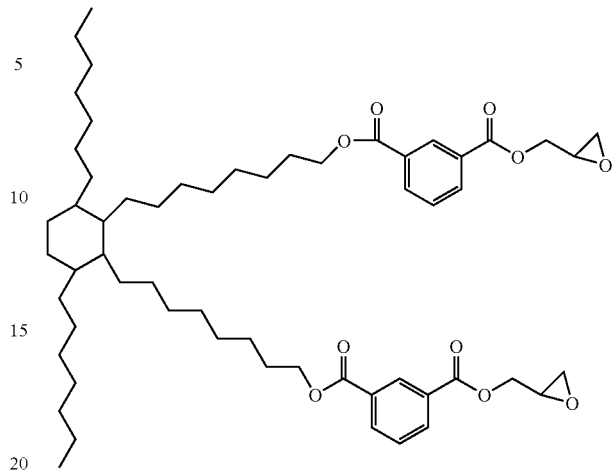

Compound 2

To a 500 mL flask was added isophthaloyl dichloride (20.3 g, 100 mmol) and toluene (100 mL). A mixture containing the dimer diol Solvermol 908 (Cognis, 26.8 g, 50 mmol) and triethylamine (15.2 g, 150 mmol) was added over a 90 min period. The reaction mixture was stirred at room temperature for 30 min and then cooled to −15° C. Glycidol (8.2 g, 110 mmol) was added to the mixture over a 20 min period. The reaction mixture was stirred at room temperature for 3 hrs. Next, the reaction mixture was washed with brine (3×50 ml) and water (3×50 mL), and then passed over MgSO$_4$ (15 g) and SiO$_2$ (15 g). Rotary evaporation of toluene afforded Compound 2 (37.3 g, 79% yield).

Example 3

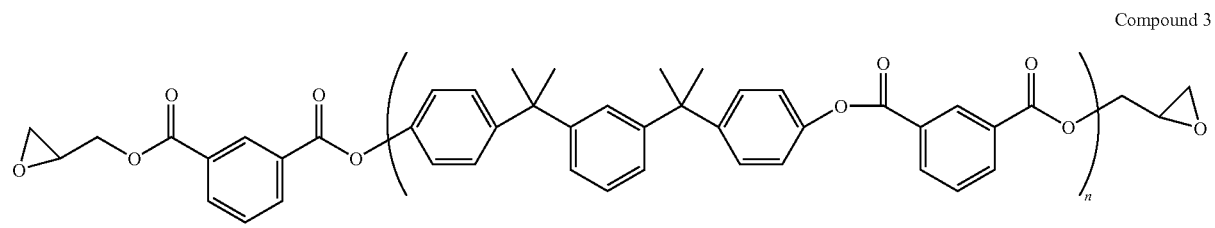

Compound 3

To a 500 mL flask was added isophthaloyl dichloride (20.3 g, 100 mmol) triethylamine (22.3 g, 220 mmol), and toluene (100 mL). A solution of bisphenol-M (26.0 g, 75 mmol) in toluene (100 mL) was added dropwise over a 10 minute period. The mixture stirred for 45 minutes, and then was cooled to 20° C. Glycidol (4.5 g, 60 mmol) was added dropwise over a 10 minute period, and the reaction was allowed to stir overnight. The reaction mixture was washed with brine (3×50 ml) and water (3×50 mL), and then passed over MgSO$_4$ (15 g) and SiO$_2$ (15 g). Toluene was removed by rotary evaporation. The product was a dried in an oven at 80° C. for 3 days to afford Compound 3 (29.6 g, 69.2% yield) as an orange, friable solid.

Example 4

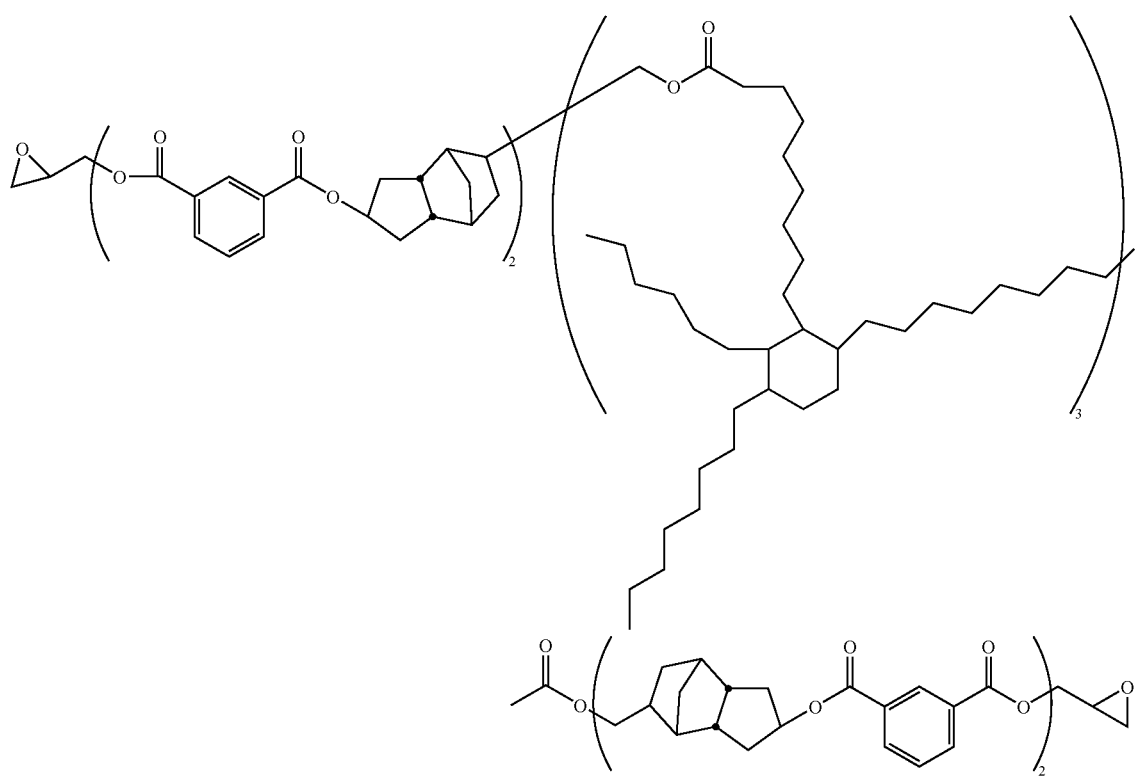

Compound 4

To a 1 L flask was added isophthalic acid (16.6 g, 100 mmol), 4,8-bis(hydroxymethyl)tricyclo[5.2.1.0$^{2,6}$]decane (39.2 g, 200 mmol), Empol 1008 (hydrogenated dimmer acid, available from Cognis) (56.5 g, 100 mmol), Pripol 2033 (Cognis, 26.8, 50 mmol) and toluene (300 mL). The reaction mixture was heated to 70° C., at which time methanesulfonic acid (5 g) was added. The flask was equipped with a reflux condenser and Dean-Stark trap, and the reaction mixture was refluxed for 20.5 hrs. After cooling, triethylamine (22.3 g, 220 mmol) and isophthaloyl dichloride (20.3 g, 100 mmol) were added and the mixture was stirred at room temperature for 3 hrs. The reaction mixture was washed with brine and water, and then passed over MgSO$_4$ and SiO$_2$ Toluene was removed by rotary evaporation and the product was dried at 80° C. for 6.5 hrs to afford Compound 4 (148.5 g, 97.5% yield)

While this invention has been described with respect to these specific examples, it should be clear that other modifications and variations would be possible without departing from the spirit of this invention.

What is claimed is:

1. A compound having the structure:

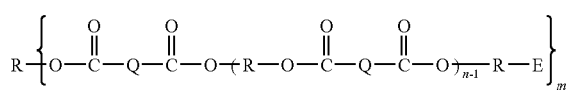

wherein:

each of R and Q is independently selected from the group consisting of substituted or unsubstituted aliphatic, alkenyl, aryl and heteroaryl moieties;

each E is independently selected from the group consisting of a ring-opening polymerizable moiety and a ring-forming polymerizable moiety;

m is an integer having the value of 3 or 4; and n is integer having the value of between 1 and about 10.

2. The compound of claim 1, wherein R is selected from the group consisting of $C_2$ to about $C_{500}$ aliphatic or alkenyl moieties.

3. The compound of claim 1, wherein R is selected from the group consisting of $C_2$ to about $C_{100}$ aliphatic or alkenyl moieties.

4. The compound of claim 1, wherein R is a $C_{36}$ aliphatic or alkenyl moiety.

5. The compound of claim 1, wherein R is selected from the group consisting of a substituted or unsubstituted cycloalkyl moieties having between 5 and about 20 carbon atoms.

6. The compound of claim 1, wherein R is selected from the group consisting of substituted or unsubstituted cyclopentyl, cyclohexyl, norbornyl, tricyclododecyl and dicyclopentadienyl moieties.

7. The compound of claim 1, wherein Q is selected from the group consisting of substituted or unsubstituted phenyl, naphthyl, cycloalkyl and or norbornenyl moieties.

8. The compound of claim 1, wherein Q is selected from the group consisting of $C_2$ to about $C_{500}$ aliphatic or alkenyl moieties.

9. The compound of claim 1, wherein Q is selected from the group consisting of $C_2$ to about $C_{100}$ aliphatic or alkenyl moieties.

10. The compound of claim 1, wherein Q is a $C_{36}$ aliphatic or alkenyl moiety.

11. The compound of claim 1, wherein the substituted aliphatic or alkeneyl, aryl and heteroaryl moieties comprise substituents selected from the group consisting of an alkyl, an alkenyl, an alkynyl, hydroxy, oxo, an alkoxy, mercapto, a cycloalkyl, a substituted cycloalkyl, a heterocyclic, a substituted heterocyclic, an aryl, a substituted aryl, a heteroaryl, a substituted heteroaryl, an aryloxy, a substituted aryloxy, a halogen, a haloalkyl, cyano, nitro, nitrone, an amino, an amido, —C(O)H, —C(O)—O—, —C(O)—, —S—, —S(O)$_2$—, —OC(O)—O—, —NR—C(O)—, —NR—C(O)—NR— and —OC(O)—NR—, wherein R is selected from the group consisting of H, a lower alkyl, an acyl, an oxyacyl, carboxyl, carbamate, sulfonyl, a sulfonamide and sulfuryl.

12. The compound of claim 1, wherein E is selected from the group consisting of epoxy, oxetane, oxazoline, benzoxazine, cyanate ester and propargyl ether.

13. A compound having the structure:

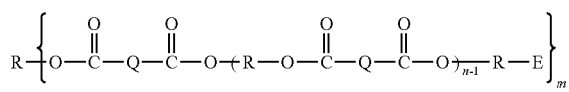

wherein:
each of R and Q is independently selected from the group consisting of substituted or unsubstituted aliphatic, alkenyl, aryl and heteroaryl moieties;
each E is independently selected from the group consisting of oxetane, oxazoline, benzoxazine, cyanate ester and propargyl ether;
m is an integer having the value of 3 or 4; and
n is integer having the value of between 1 and about 10.

14. The compound of claim 13, wherein R is selected from the group consisting of $C_2$ to about $C_{500}$ aliphatic or alkenyl moieties.

15. The compound of claim 13, wherein R is selected from the group consisting of $C_2$ to about $C_{100}$ aliphatic or alkenyl moieties.

16. The compound of claim 13, wherein R is a $C_{36}$ -aliphatic or alkenyl moiety.

17. The compound of claim 13, wherein R is selected from the group consisting of substituted or unsubstituted cycloalkyl moieties having between 5 and about 20 carbon atoms.

18. The compound of claim 13, wherein R is selected from the group consisting of substituted or unsubstituted cyclopentyl, cyclohexyl, norbornyl, tricyclododecyl and dicyclopentadienyl moieties.

19. The compound of claim 13, wherein Q is selected from the group consisting of substituted or unsubstituted phenyl, naphthyl, cycloalkyl and or norbornenyl moieties.

20. The compound of claim 13, wherein Q is selected from the group consisting of $C_2$ to about $C_{500}$ aliphatic or alkenyl moieties.

21. The compound of claim 13, wherein Q is selected from the group consisting of $C_2$ to about $C_{100}$ aliphatic or alkenyl moieties.

22. The compound of claim 13, wherein Q is a $C_{36}$ aliphatic or alkenyl moiety.

23. The compound of claim 13, wherein the substituted aliphatic or alkeneyl, aryl and heteroaryl moieties comprise substituents selected from the group consisting of an alkyl, an alkenyl, an alkynyl, hydroxy, oxo, an alkoxy, mercapto, a cycloalkyl, a substituted cycloalkyl, a heterocyclic, a substituted heterocyclic, an aryl, a substituted aryl, a heteroaryl, a substituted heteroaryl, an aryloxy, a substituted aryloxy, a halogen, a haloalkyl, cyano, nitro, nitrone, an amino, an amido, —C(O)H, —C(O)—O—, —C(O)—, —S—, —S(O)$_2$—, —OC(O)—O—, —NR—C(O)—, —NR—C(O)—NR— and —OC(O)—NR—, wherein R is selected from the group consisting of H, a lower alkyl, an acyl, an oxyacyl, carboxyl, carbamate, sulfonyl, a sulfonamide and sulfuryl.

* * * * *